(12) United States Patent
Andjelkovic et al.

(10) Patent No.: US 8,039,487 B2
(45) Date of Patent: Oct. 18, 2011

(54) PIPERIDINE-AMIDE DERIVATIVES

(75) Inventors: Mirjana Andjelkovic, Basel (CH);
Simona M. Ceccarelli, Basel (CH);
Odile Chomienne, Altkirch (FR);
Patrizio Mattei, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 817 days.

(21) Appl. No.: 12/125,976

(22) Filed: May 23, 2008

(65) Prior Publication Data

US 2008/0300279 A1    Dec. 4, 2008

(30) Foreign Application Priority Data

Jun. 1, 2007  (EP) .................................... 07109458

(51) Int. Cl.
*C07D 401/04* (2006.01)
*C07D 401/14* (2006.01)
*A61K 31/4535* (2006.01)
*A61K 31/4545* (2006.01)
*A61P 3/00* (2006.01)
*A61P 9/00* (2006.01)

(52) U.S. Cl. ......... 514/318; 514/326; 546/201; 546/209
(58) Field of Classification Search .................. None
See application file for complete search history.

(56) References Cited

U.S. PATENT DOCUMENTS

| 7,645,776 B2 * | 1/2010 | Ackermann et al. .......... 514/326 |
| 7,767,819 B2 * | 8/2010 | Guedat et al. ................. 546/209 |
| 2007/0129544 A1 | 6/2007 | Ackermann et al. |
| 2011/0060007 A1 * | 3/2011 | Leriche et al. ................ 514/314 |
| 2011/0105505 A1 * | 5/2011 | Stieber et al. ............. 514/236.8 |

FOREIGN PATENT DOCUMENTS

| WO | WO 2005/074934 | * | 8/2005 |
| WO | WO 2006/131452 |   | 12/2006 |

* cited by examiner

*Primary Examiner* — Fiona T Powers
(74) *Attorney, Agent, or Firm* — George W. Johnston; Dennis P. Tramaloni; Brian C. Remy

(57) ABSTRACT

The invention is concerned with novel piperidine-amide derivatives of formula (I)

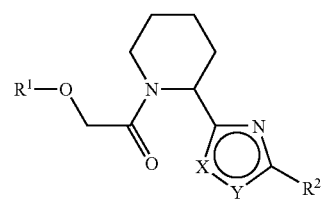

wherein $R^1$, $R^2$, X and Y are as defined in the description and in the claims, as well as physiologically acceptable salts and esters thereof. These compounds inhibit L-CPT1 and may be used to treat diseases associated with L-CPT1.

21 Claims, No Drawings ic syndrome, hyperlipidemia, hypercholesterolemia, fatty liver disease, atherosclerosis, congestive heart failure and renal failure.

PIPERIDINE-AMIDE DERIVATIVES

PRIORITY TO RELATED APPLICATION(S)

This application claims the benefit of European Patent Application No. 07109458.5, filed Jun. 1, 2007, which is hereby incorporated by reference in its entirety.

BACKGROUND OF THE INVENTION

The present invention relates to novel piperidine-amide, their manufacture, pharmaceutical compositions containing them and their use as medicaments. The active compounds of the present invention are inhibitors of liver carnitine palmitoyl transferase 1 (L-CPT1) activity.

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-terminal domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates pyruvate carboxylase and gluconeogenesis. According to the mechanism of action described above, pharmaceutically active substances which inhibit L-CPT1 reduce liver β-oxidation, consequently inhibiting gluconeogenesis and therefore counteract hyperglycemia.

SUMMARY OF THE INVENTION

The invention is concerned with the compounds of formula (I):

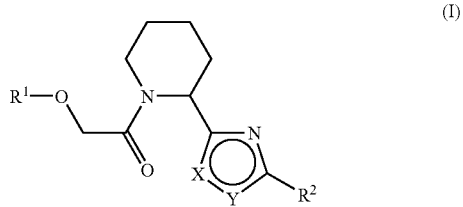

and pharmaceutically acceptable salts and esters thereof, wherein X, Y, R$^1$ and R$^2$ are as defined in the detailed description and claims. In addition, the present invention relates to the methods of manufacturing and using the compounds of formula I as well as pharmaceutical compositions containing them. The compounds of formula I are inhibitors of liver carnitine palmitoyl transferase 1 (L-CPT1) activity. The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include, for example, diabetes and associated pathologies, non insulin dependent diabetes mellitus (also referred to as diabetes type II), obesity, hypertension, insulin resistance syndrome, meta-

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atom(s). In preferred embodiments, the group contains of one to four carbon atom(s).

The term "halogen" refers to fluorine, chlorine, bromine or iodine. In certain preferred embodiments, the halogen is fluorine, chlorine or bromine.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring. Examples of an amino group include —NH$_2$, methylamino, ethylamino, dimethylamino, diethylamino, methyl-ethylamino, pyrrolidin-1-yl and piperidino; preferably the amino group is a primary amino, dimethylamino, or diethylamino.

The term "alkyl", alone or in combination with other groups, refers to a branched or straight-chain monovalent saturated aliphatic hydrocarbon radical of one to twenty carbon atoms. In certain preferred embodiments, the alkyl has one to sixteen carbon atoms, and more preferably one to ten carbon atoms. Lower-alkyl groups as described below also are preferred alkyl groups. Alkyl groups can optionally be substituted with hydroxy, —COOH, carbamoyl, amino, halogen or lower-alkoxy. Unsubstituted alkyl groups are preferred.

The term "lower-alkyl", alone or in combination with other groups, refers to a branched or straight-chain monovalent alkyl radical of one to seven carbon atoms. In certain preferred embodiments, the lower-alkyl has one to four carbon atoms. This term is further exemplified by such radicals as methyl, ethyl, n-propyl, isopropyl, n-butyl, s-butyl, t-butyl and the like. Lower-alkyl groups can optionally be substituted with hydroxy, —COOH, carbamoyl, amino, halogen or lower-alkoxy. Unsubstituted lower-alkyl groups are preferred.

The term "cycloalkyl" refers to a monovalent carbocyclic radical of 3 to 10 carbon atoms. In certain preferred embodiments, the cycloalkyl has 3 to 6 carbon atoms, such as cyclopropyl, cyclobutyl, cyclopentyl, and cyclohexyl.

The term "fluoro-lower-alkyl" refers to lower-alkyl groups which are mono- or multiply substituted with fluorine. Examples of fluoro-lower-alkyl groups include CFH$_2$, CF$_2$H, CF$_3$, CF$_3$CH$_2$, CF$_3$(CH$_2$)$_2$, (CF$_3$)$_2$CH and CF$_2$H—CF$_2$.

The term "alkoxy" refers to the group R'—O—, wherein R' is an alkyl. The term "lower-alkoxy" refers to the group R'—O—, wherein R' is a lower-alkyl. Alkoxy or lower-alkoxy groups can optionally be substituted as defined above in context with the definition of alkyl and lower-alkyl respectively. Unsubstituted alkoxy or lower-alkoxy groups are preferred.

The term "fluoro-lower-alkoxy" refers to the group R"—O—, wherein R" is fluoro-lower-alkyl. Examples of fluoro-lower-alkoxy groups include CFH$_2$—O, CF$_2$H—O, CF$_3$—O, CF$_3$CH$_2$—O, CF$_3$(CH$_2$)$_2$—O, (CF$_3$)$_2$CH—O, and CF$_2$H—CF$_2$—O.

The term "aryl", alone or in combination with other groups, relates to the phenyl or naphthyl group which can optionally be substituted, unless specifically stated otherwise, by 1 to 5 substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, (H,lower-alkyl)NC(O), (lower-alkyl)$_2$NC(O), fluoro-lower-alkyl, fluoro-lower-alkoxy, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, cycloalkyl, phenyl and phenyloxy. In certain preferred embodiments, the aryl group is the phenyl group and in certain preferred embodiments the aryl group is optionally substituted by 1 to 3 substituents selected from the group consisting of halogen, lower-alkyl and lower-alkoxy. Furthermore, aryl groups can preferably be substituted as described in the description and claims.

The term "heteroaryl" refers to an aromatic, optionally partially saturated, 5 to 6 membered monocyclic ring or 9 to 10 membered bicyclic ring which can comprise 1, 2 or 3 heteroatoms independently selected from nitrogen, oxygen and sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzoisothiazolyl, benzoxazolyl, benzoisoxazolyl, quinolinyl, 1,3-dihydroindolyl-2-one, benzo[1,3]dioxol-5-yl and 2,3-dihydro-benzo[1,4]dioxinyl. Unless specifically stated otherwise, a heteroaryl group may optionally have a substitution pattern as described earlier in connection with the term "aryl". Furthermore, heteroaryl groups can preferably be substituted as described in the description below.

Compounds of formula (I) which carry an acidic group, such as a —COOH group, can form pharmaceutically acceptable salts with physiologically compatible bases. Examples of such salts are alkaline, earth-alkaline and ammonium salts such as sodium, potassium, calcium and trimethylammonium salt. The term "pharmaceutically acceptable salts" refers to such salts. Compounds of formula (I) which carry a suitable basic group, such as an amino group, can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" also refers to such salts.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to compounds of formula (I):

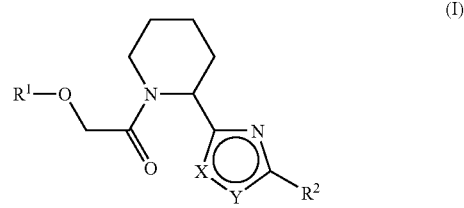

and pharmaceutically acceptable salts and esters thereof wherein:

X is sulfur and Y is —$CR^3$, or alternatively, X is —$CR^3$ and Y is sulfur; and $R^3$ is hydrogen, halogen, —CN, lower-alkyl, fluoro-lower-alkyl, lower-alkoxy, fluoro-lower-alkoxy or lower-alkoxy-lower-alkyl;

$R^1$ is aryl or heteroaryl, which aryl or heteroaryl can optionally be substituted with 1 to 3 substituents independently selected from the group consisting of halogen, hydroxy, —CN, lower-alkyl and hydroxy-lower-alkyl;

R² is aryl, heteroaryl or aryl-lower-alkyl, wherein said aryl or heteroaryl can optionally be substituted with 1 to 3 substituents independently selected from the group consisting of:
(1) lower-alkyl, optionally substituted with hydroxy, —COOH, carbamoyl, amino, halogen or lower-alkoxy,
(2) halogen,
(3) hydroxy,
(4) —CN,
(5) —NO₂,
(6) fluoro-lower-alkyl,
(7) lower-alkoxy, optionally substituted with hydroxy, —COOH, carbamoyl, amino, halogen or lower-alkoxy,
(8) fluoro-lower-alkoxy,
(9) —S(O₂)R⁴, wherein R⁴ is lower-alkyl or amino;
(10) —C(O)R⁵, wherein R⁵ is hydrogen, hydroxy, lower-alkyl, lower-alkoxy or amino;
(11) imidazolyl,
(12) pyrazolyl,
(13) tetrazolyl,
(14) pyrrolyl, and
(15) —NR⁶R⁷, wherein R⁶ and R⁷, independently from each other, are selected from the group consisting of hydrogen, lower-alkyl, lower-alkyl-carbonyl and lower-alkyl-SO₂.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) have one or more asymmetric carbon atoms and can therefore exist as an enantiomeric mixture, mixture of stereoisomers or as optically pure compounds.

A preferred embodiment of the present invention relates to compounds of formula (I) as described above, wherein X is sulfur, Y is —CR³ and R³ is as defined above. Other preferred compounds are those, wherein X is —CR³, Y is sulfur and R³ is as defined above.

Preferred compounds of formula (I) according to the present invention are those, wherein R¹ is aryl, particularly wherein R¹ is phenyl.

In a preferred embodiment according to the present invention, R² is phenyl, benzyl or a heteroaryl selected from the group consisting of pyridinyl, 1,3-dihydroindolyl-2-one, benzo[1,3]dioxol-5-yl, indolyl, thienyl, indazolyl, pyrazinyl and 2,3-dihydro-benzo[1,4]dioxinyl, which phenyl, benzyl or heteroaryl is optionally substituted with 1 to 3 substituents independently selected from the group consisting of lower-alkyl, halogen, hydroxy, —CN, fluoro-lower-alkyl, lower-alkoxy, fluoro-lower-alkoxy, —S(O₂)R⁴, —C(O)R⁵ and —NR⁶R⁷, wherein R⁴, R⁵, R⁶ and R⁷ are as defined above. More preferably, R² is phenyl or a heteroaryl selected from the group consisting of pyridinyl and 1,3-dihydroindolyl-2-one, which phenyl or heteroaryl is optionally substituted with —C(O)R⁵ or —NR⁶R⁷, wherein R⁵, R⁶ and R⁷ are as defined above. Even more preferably, R² is 4-carboxy-phenyl, 3-carboxy-phenyl, 4-acetamide-phenyl, pyridin-2-yl, pyridin-3-yl, 1,3-dihydroindol-2-one-5-yl or 3-carboxy-pyridin-2-yl.

Other preferred compounds of formula (I) as defined above are those, wherein R³ is hydrogen or lower-alkyl, particularly wherein R³ is hydrogen. Furthermore, it is preferred that R⁴ is lower-alkyl.

A further preferred embodiment of the present invention refers to compounds of formula (I) as defined above, wherein R⁵ is hydroxy, lower-alkoxy or amino. More preferably, R⁵ is hydroxy.

Other preferred compounds of the present invention are those, wherein R⁶ and R⁷ independently from each other are hydrogen, lower-alkyl or lower-alkyl-carbonyl, particularly wherein R⁶ and R⁷, independently from each other, are hydrogen or lower-alkyl-carbonyl. Preferably, R⁶ is hydrogen. Preferably, R⁷ is acetyl.

A further preferred embodiment of the present invention is related to compounds as defined above, which are R-enantiomers and which are characterised by formula (Ia):

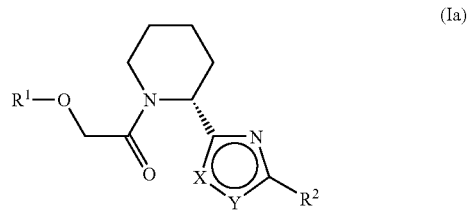

(Ia)

wherein R¹, R², X and Y are as defined above.

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:
1-{(R)-2-[4-(4-Chloro-phenyl)-thiazol-2-yl]-piperidin-1-yl}-2-phenoxy-ethanone,
2-Phenoxy-1-[(R)-2-(4-phenyl-thiazol-2-yl)-piperidin-1-yl]-ethanone,
4-{2-[(R)-1-(2-Phenoxy-acetyl)-piperidin-2-yl]-thiazol-4-yl}-benzoic acid,
2-Phenoxy-1-{(R)-2-[4-(4-trifluoromethoxy-phenyl)-thiazol-2-yl]-piperidin-1-yl}-ethanone,
3-{2-[(R)-1-(2-Phenoxy-acetyl)-piperidin-2-yl]-thiazol-4-yl}-benzoic acid,
2-Phenoxy-1-[(R)-2-(4-pyridin-2-yl-thiazol-2-yl)-piperidin-1-yl]-ethanone,
1-{(R)-2-[4-(3,4-Difluoro-phenyl)-thiazol-2-yl]-piperidin-1-yl}-2-phenoxy-ethanone,
2-Phenoxy-1-[(R)-2-(4-pyridin-3-yl-thiazol-2-yl)-piperidin-1-yl]-ethanone,
1-{(R)-2-[4-(5-Chloro-2-methoxy-phenyl)-thiazol-2-yl]-piperidin-1-yl}-2-phenoxy-ethanone,
2-Phenoxy-1-[(R)-2-(4-pyridin-4-yl-thiazol-2-yl)-piperidin-1-yl]-ethanone,
1-{(R)-2-[4-(2-Methoxy-phenyl)-thiazol-2-yl]-piperidin-1-yl}-2-phenoxy-ethanone,
1-{(R)-2-[4-(4-Methanesulfonyl-phenyl)-thiazol-2-yl]-piperidin-1-yl}-2-phenoxy-ethanone,
6-{2-[(R)-1-(2-Phenoxy-acetyl)-piperidin-2-yl]-thiazol-4-yl}-pyridine-2-carboxylic acid methyl ester,
5-{2-[(R)-1-(2-Phenoxy-acetyl)-piperidin-2-yl]-thiazol-4-yl}-1,3-dihydro-indol-2-one,
N-(4-{2-[(R)-1-(2-Phenoxy-acetyl)-piperidin-2-yl]-thiazol-4-yl}-phenyl)-acetamide,
1-{(R)-2-[4-(4-Hydroxy-phenyl)-thiazol-2-yl]-piperidin-1-yl}-2-phenoxy-ethanone, 1-[(R)-2-(4-Benzo[1,3]dioxol-5-yl-thiazol-2-yl)-piperidin-1-yl]-2-phenoxy-ethanone,
1-{(R)-2-[4-(4-Dimethylamino-phenyl)-thiazol-2-yl]-piperidin-1-yl}-2-phenoxy-ethanone,
1-{(R)-2-[4-(3-Methyl-1H-indol-2-yl)-thiazol-2-yl]-piperidin-1-yl}-2-phenoxy-ethanone,
4-{2-[(R)-1-(2-Phenoxy-acetyl)-piperidin-2-yl]-thiazol-4-yl}-benzonitrile,
3-{2-[(R)-1-(2-Phenoxy-acetyl)-piperidin-2-yl]-thiazol-4-yl}-benzonitrile,
1-{(R)-2-[4-(6-Chloro-pyridin-3-yl)-thiazol-2-yl]-piperidin-1-yl}-2-phenoxy-ethanone,
1-{(R)-2-[4-(5-Bromo-thiophen-2-yl)-thiazol-2-yl]-piperidin-1-yl}-2-phenoxy-ethanone,
3-{4-[(R)-1-(2-Phenoxy-acetyl)-piperidin-2-yl]-thiazol-2-yl}-benzoic acid methyl ester,
N-(4-{4-[(R)-1-(2-Phenoxy-acetyl)-piperidin-2-yl]-thiazol-2-yl}-phenyl)-acetamide,
1-{(R)-2-[2-(1H-Indazol-3-yl)-thiazol-4-yl]-piperidin-1-yl}-2-phenoxy-ethanone,
2-Phenoxy-1-{(R)-2-[2-(6-trifluoromethyl-pyridin-3-yl)-thiazol-4-yl]-piperidin-1-yl}-ethanone,
2-Phenoxy-1-{(R)-2-[2-(5-trifluoromethyl-pyridin-2-yl)-thiazol-4-yl]-piperidin-1-yl}-ethanone,
2-Phenoxy-1-[(R)-2-(2-pyrazin-2-yl-thiazol-4-yl)-piperidin-1-yl]-ethanone,
1-{(R)-2-[2-(6-Methyl-pyridin-3-yl)-thiazol-4-yl]-piperidin-1-yl}-2-phenoxy-ethanone,
2-Phenoxy-1-[(R)-2-(2-pyridin-3-yl-thiazol-4-yl)-piperidin-1-yl]-ethanone,
2-Phenoxy-1-[(R)-2-(2-pyridin-4-yl-thiazol-4-yl)-piperidin-1-yl]-ethanone,
1-{(R)-2-[2-(6-Methoxy-pyridin-3-yl)-thiazol-4-yl]-piperidin-1-yl}-2-phenoxy-ethanone,
2-Phenoxy-1-[(R)-2-(2-pyridin-2-yl-thiazol-4-yl)-piperidin-1-yl]-ethanone,
1-{(R)-2-[2-(4-Fluoro-phenyl)-thiazol-4-yl]-piperidin-1-yl}-2-phenoxy-ethanone,
4-{4-[(R)-1-(2-Phenoxy-acetyl)-piperidin-2-yl]-thiazol-2-yl}-benzoic acid methyl ester,
1-{(R)-2-[2-(4-Chloro-benzyl)-thiazol-4-yl]-piperidin-1-yl}-2-phenoxy-ethanone,
1-{(R)-2-[2-(2,3-Dihydro-benzo[1,4]dioxin-2-yl)-thiazol-4-yl]-piperidin-1-yl}-2-phenoxy-ethanone,
4-{2-[(R)-1-(2-Phenoxy-acetyl)-piperidin-2-yl]-thiazol-4-yl}-benzamide,
3-{4-[(R)-1-(2-Phenoxy-acetyl)-piperidin-2-yl]-thiazol-2-yl}-benzoic acid,
4-{4-[(R)-1-(2-Phenoxy-acetyl)-piperidin-2-yl]-thiazol-2-yl}-benzoic acid,
6-{2-[(R)-1-(2-Phenoxy-acetyl)-piperidin-2-yl]-thiazol-4-yl}-pyridine-2-carboxylic acid,
Sodium; 4-{2-[(R)-1-(2-phenoxy-acetyl)-piperidin-2-yl]-thiazol-4-yl}-benzoate,
Sodium; 3-{2-[(R)-1-(2-phenoxy-acetyl)-piperidin-2-yl]-thiazol-4-yl}-benzoate,
3-{5-Methyl-2-[(R)-1-(2-phenoxy-acetyl)-piperidin-2-yl]-thiazol-4-yl}-benzoic acid methyl ester, and
3-{5-Methyl-2-[(R)-1-(2-phenoxy-acetyl)-piperidin-2-yl]-thiazol-4-yl}-benzoic acid,
and pharmaceutically acceptable salts and esters thereof.

Particularly preferred compounds of formula (I) are those selected from the group consisting of:
4-{2-[(R)-1-(2-Phenoxy-acetyl)-piperidin-2-yl]-thiazol-4-yl}-benzoic acid,
3-{2-[(R)-1-(2-Phenoxy-acetyl)-piperidin-2-yl]-thiazol-4-yl}-benzoic acid,
2-Phenoxy-1-[(R)-2-(4-pyridin-2-yl-thiazol-2-yl)-piperidin-1-yl]-ethanone,
2-Phenoxy-1-[(R)-2-(4-pyridin-3-yl-thiazol-2-yl)-piperidin-1-yl]-ethanone,
5-{2-[(R)-1-(2-Phenoxy-acetyl)-piperidin-2-yl]-thiazol-4-yl}-1,3-dihydro-indol-2-one,
N-(4-{2-[(R)-1-(2-Phenoxy-acetyl)-piperidin-2-yl]-thiazol-4-yl}-phenyl)-acetamide,
2-Phenoxy-1-[(R)-2-(2-pyridin-3-yl-thiazol-4-yl)-piperidin-1-yl]-ethanone,
3-{4-[(R)-1-(2-Phenoxy-acetyl)-piperidin-2-yl]-thiazol-2-yl}-benzoic acid,
6-{2-[(R)-1-(2-Phenoxy-acetyl)-piperidin-2-yl]-thiazol-4-yl}-pyridine-2-carboxylic acid, and
3-{2-[(R)-1-(2-phenoxy-acetyl)-piperidin-2-yl]-thiazol-4-yl}-benzoate sodium salt,
and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (IV):

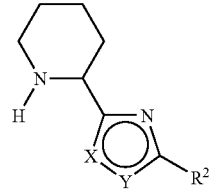

(IV)

with a compound of formula $R^1$—O—$CH_2$—C(O)Cl, wherein $R^1$, $R^2$, X and Y are as defined above.

The reaction of a compound of formula (IV) with a compound of formula $R^1$—O—$CH_2$—C(O)Cl can be carried out under conditions well known to the person skilled in the art. For example, the compound of formula (IV) is reacted with a compound of formula $R^1$—O—$CH_2$—C(O)Cl in anhydrous solvents such as dichloromethane, tetrahydrofuran, acetonitrile, toluene and mixtures thereof or in the absence of solvent, at temperatures between 0° C. and 110° C., optionally in the presence of a base like triethylamine, diisopropylethylamine or pyridine.

The present invention also relates to compounds of formula (I) as defined above, when prepared by a process as described above.

The compounds of formula (IV) and $R^1$—O—$CH_2$—C(O)Cl can be prepared by methods known in the art or as described below or in analogy thereto. Unless otherwise indicated, $R^1$, $R^2$, X and Y are as described above.

Compounds of formula (I), where X is sulfur and Y is —$CR^3$ are part of the present invention and are represented by general formula (II):

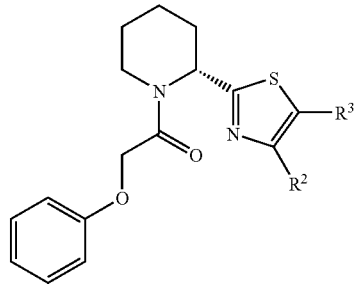

(II)

Compounds of general formula (II) can be accessed as detailed in scheme 1.

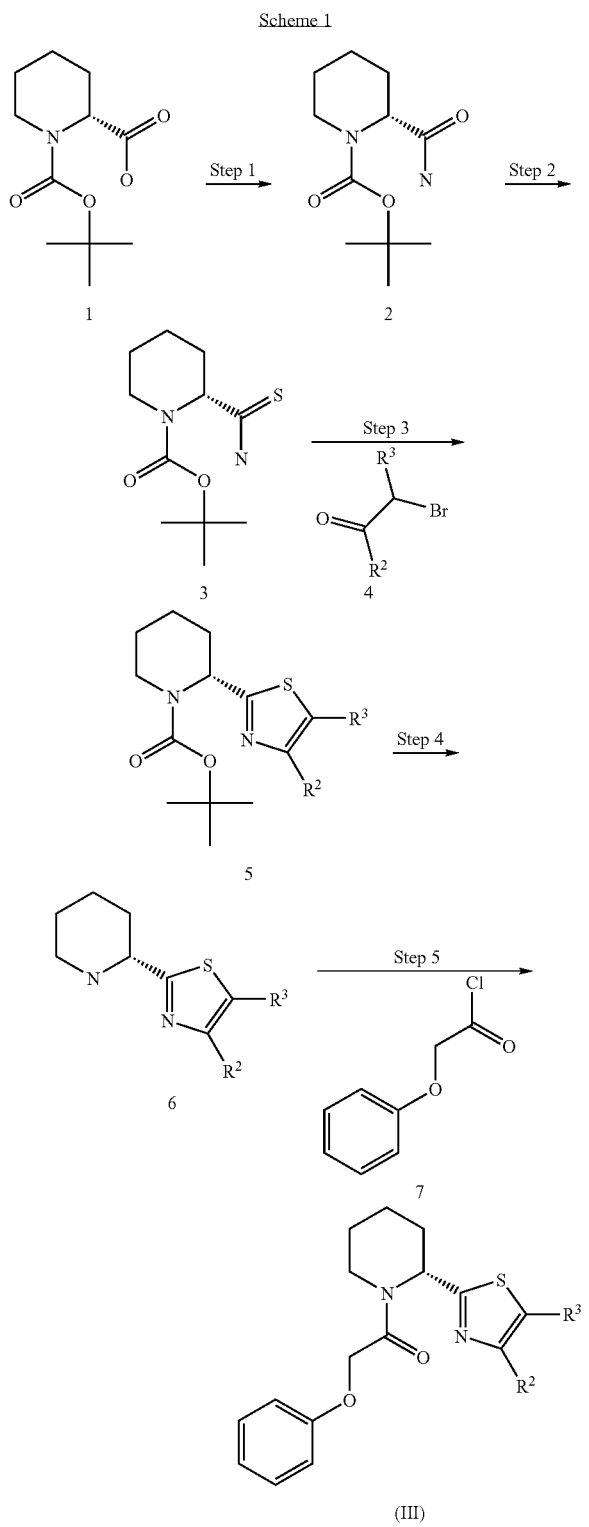

Scheme 1

In step 1, scheme 1, (R)-(+)-piperidine-1,2-dicarboxylic acid 1-tert-butyl ester 1 is converted to the corresponding primary amide 2 by methods well known to somebody skilled in the art, namely by condensation with an ammonia equivalent. Typical reaction conditions involve mixing of acid 1 with ammonium chloride or another ammonia equivalent under basic conditions in the presence of a condensing agent and eventual intermediacy of an activated ester, anhydride or acyl chloride. Typically used bases are diisopropylethylamine, triethylamine, pyridine, 4-dimethylaminopyridine, morpholine or other organic base. Typically used condensing reagents are for example O-(7-benzotriazol-1-yl)-N,N,N',N'-tetramethyluronium-tetrafluoroborate (TBTU), O-(7-azabenzotriazol-1-yl)-N,N,N',N'-tetramethyluronium-hexaflurophophate (HATU), N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluorophosphate, bromo-tris-pyrrolidino-phosphonium hexafluorophosphate, carbonyl diimidazole or others well known to the person skilled in the art. The reaction is usually carried out in aprotic solvents such as dichloromethane, tetrahydrofuran, N,N-dimethylformamide, N,N-dimethylacetamide, N-methylpyrrolidinone and mixtures thereof at temperatures between 0° C. and 60° C. Alternatively, such reactions can be performed in two steps involving first formation of the acyl halide derivative of the acid 1 and subsequent coupling reaction with an ammonium equivalent in the presence of a base. Typically employed reagents for the formation of the acyl chloride are thionyl chloride, phosphorous pentachloride, oxalyl chloride, chloroformiates or cyanuric chloride, and the reaction is generally conducted in the absence of a solvent or in the presence of an aprotic solvent like dichloromethane, toluene or acetone. A base can optionally be added, like for example pyridine, triethylamine, diisopropyl ethyl amine or N-methyl morpholine. The obtained acyl chloride can be isolated or reacted as such with an appropriate ammonium equivalent in an aprotic solvent, like dichloromethane, tetrahydrofuran or acetone, in the presence of a base. Typical bases are triethylamine, 4-methylmorpholine, pyridine, diisopropyl ethyl amine or dimethylaminopyridine or mixtures thereof. In step 2, scheme 1, the amide 2 is converted to the corresponding thioamide 3 according to methods well known to somebody skilled in the art, namely by reaction with 2,4-bis(4-methoxyphenyl)-1,3,2,4-dithiadiphosphetane 2,4-disulfide (Lawesson's reagent). In step 3, scheme 1, the obtained thioamide 3 is reacted with aptly substituted α-bromoketones 4 to yield the corresponding thiazoles 5 according to methods well known to people skilled in the art, namely cyclocondensation. The reaction can be carried out under a variety of conditions favoring the elimination of hydrogen bromide and water. Typically used conditions involve a two stage reaction between the thioamide 3 and the α-bromoketone 4 at temperature between 0 and 100° C., followed by dehydration with trifluoracetic anhydride and pyridine at temperatures between 0 and 50° C. In step 4, scheme 1, the obtained thiazoles of general formula 5 are deprotected to yield the free piperidines 6, by methods well known to somebody skilled in the art, namely by treatment of the BOC-protected piperdines 5 with organic or mineral acid in the absence of a solvent or in the presence of a suitable organic solvent. Typically used acids are hydrochloric acid and trifluoroacetic acid in solvents such as dichloromethane, dioxane, tetrahydrofurane, ether or alcoholic solvents. In step 5, scheme 1, the obtained free piperidine 6 is reacted with phenoxyacetyl chloride 7 under standard conditions to yield compounds of general formula (II). Typically used reaction conditions involve mixing the piperidines 6 with the acyl chloride 7 in an aprotic solvent, like dichloromethane, tetrahydrofuran or acetone, in the presence of a base. Typical bases are triethylamine, 4-methylmorpholine, pyridine, diisopropyl ethyl amine or dimethylaminopyridine or mixtures thereof.

Compounds of formula (I) where X is CR³ and Y is sulfur are part of the present invention and are represented by general formula (III):

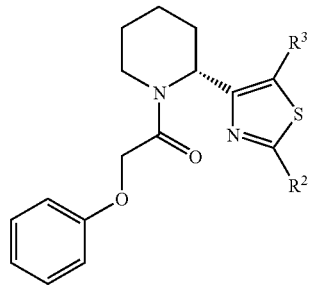

(III)

Compounds of general formula (III) can be accessed as detailed in scheme 2.

Scheme 2

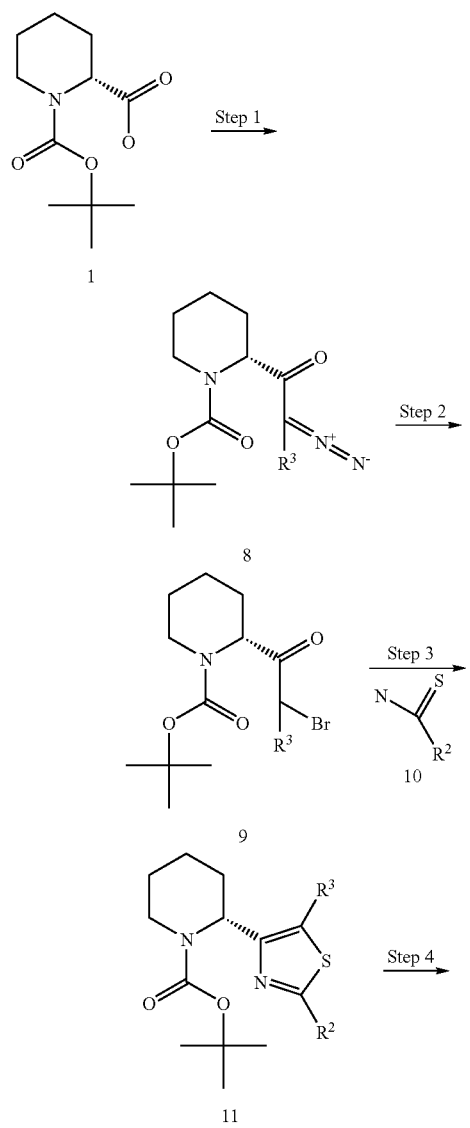

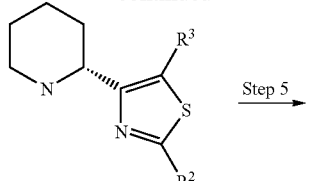

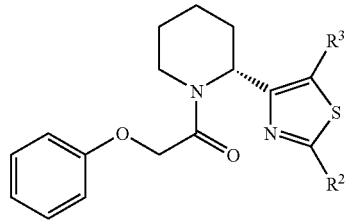

In step 1, scheme 2, (R)-(+)-piperidine-1,2-dicarboxylic acid 1-tert-butyl ester 1 is converted to the corresponding acyl chloride according to methods well known to someone skilled in the art. In particular, methods applicable to compounds containing an acid labile tert-butoxycarbonyl group have to be applied. Typically used conditions involve reactions with a chloroformate, like for example isobutyl chloroformate, in the presence of a base like for example pyridine, triethylamine, diisopropyl ethyl amine or N-methyl morpholine. The reaction is carried out either with no solvent or in the presence of an aprotic solvent like tetrahydrofurane, dichloromethane, toluene or acetone, at temperatures between −20 and 30° C. The obtained acyl chloride is not isolated but reacted directly with a diazoalkane derivative to generate the corresponding diazoketone 8. As diazoalkane derivative, the safer trimethylsilyldiazoalkanes can be used. In step 2, scheme 2, the obtained diazoketone 8 is converted to the α-bromoketone 9 by reaction with substoichiometric quantity of bromidric acid in acetic acid. In step 3, scheme 2, the obtained α-bromoketones of general formula 9 are condensed with thioamides 10 in analogy to step 3, scheme 1. In step 4, scheme 2, the obtained thiazoles 11 are deprotected to the free piperidine derivatives of general formula 12 in analogy to step 4, scheme 1. In step 5, scheme 2, the free piperidines of general formula 12 are reacted with phenoxyacetyl chloride to yield compounds of general formula (III) in analogy to step 5, scheme 1.

The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization. Salts of compounds of formula (I) with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxtris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, Biochem. J. 341, 483-489 and Jackson et al., 2000, J. Biol. Chem. 275, 19560-19566.

Human liver and muscle CPT1 cDNAs and rat CPT2 cDNA were subcloned in pGAPZB or pGAPZA, respectively. These plasmids were used to transform P. pastoris strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 µM) and palmitoyl-CoA (80 µM) reduced DTNB (300 µM) forming 5-mercapto-(2-nitrobenzoic acid) which absorbed at 410 nm with a molar extinction coefficient of 13600 $M^{-1}cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an $IC_{50}$ value below 10 uM, preferably 10 nM to 10 uM, more preferably 10 mM to 5 uM. The following table shows data for the examples.

| Example | L-CPT1 inhibition $IC_{50}$ [µmol/l] |
|---|---|
| 1 | 1.4 |
| 2 | 0.2679 |
| 3 | 0.1292 |
| 4 | 0.7976 |
| 5 | 0.0335 |
| 6 | 0.0196 |
| 7 | 0.2859 |
| 8 | 0.025 |
| 9 | 0.2472 |
| 10 | 0.068 |
| 11 | 0.2723 |
| 12 | 0.1406 |
| 13 | 0.0424 |
| 14 | 0.0659 |
| 15 | 0.0326 |
| 16 | 0.0796 |
| 17 | 0.1338 |
| 18 | 0.4201 |
| 19 | 0.3297 |

-continued

| Example | L-CPT1 inhibition IC$_{50}$ [μmol/l] |
|---|---|
| 20 | 0.0405 |
| 21 | 0.065 |
| 22 | 0.095 |
| 23 | 0.0886 |
| 24 | Nd |
| 25 | 0.1641 |
| 26 | 0.13 |
| 27 | 0.3125 |
| 28 | 0.9346 |
| 29 | 0.224 |
| 30 | 0.0887 |
| 31 | 0.0562 |
| 32 | 0.1504 |
| 33 | 0.0794 |
| 34 | 0.1755 |
| 35 | 0.1554 |
| 36 | 0.3647 |
| 37 | 0.7251 |
| 38 | 0.3982 |
| 39 | 0.2394 |
| 40 | 0.0803 |
| 41 | 0.2955 |
| 42 | 0.0377 |
| 43 | Nd |
| 44 | 0.0241 |
| 45 | 0.3 |
| 46 | 0.1 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on the severity of the disease and the precise pharmacokinetic profile the compound could be administered with one or several daily dosage units, for example, in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner. MS=mass spectrometry.

EXAMPLES

Example 1

1-{(R)-2-[4-(4-Chloro-phenyl)-thiazol-2-yl]-piperidin-1-yl}-2-phenoxy-ethanone

The title compound was prepared as illustrated in scheme 1, steps 1 to 5.

Step 1. A suspension of ammonium chloride (3.44 g, 64 mmol) in N,N-dimethylacetamide (150 mL) under argon was treated with diisopropylethylamine (13.44 g, 17.7 mL, 104 mmol). A solution of (R)-(+)-piperidine-1,2-dicarboxylic acid 1-tert-butyl ester (5.10 g, 22 mmol) was added, followed by TBTU (10.11 g, 31 mmol). The mixture was stirred at room temperature for 1.5 h, then diluted with ethyl acetate (850 mL) and washed several times with water (5*50 mL) and finally with saturated sodium chloride. The organic phase was dried over sodium sulphate and evaporated. The resulting oil was purified by flash chromatography (heptane/ethyl acetate gradient) to yield (R)-2-carbamoyl-piperidine-1-carboxylic acid tert-butyl ester (4.54 g, 89%) as a white solid, MS (ISP): 229.0 (M+H)$^{+}$.

Step 2. A solution of (R)-2-carbamoyl-piperidine-1-carboxylic acid tert-butyl ester (1.31 g, 6 mmol) in dioxane (20 mL) was treated under argon with Lawesson's reagent (1.16 g, 3 mmol). The mixture was stirred at room temperature overnight. The volatiles were evaporated and the resulting white solid purified by flash chromatography (heptane/ethyl acetate gradient) to yield (R)-2-thiocarbamoyl-piperidine-1-carboxylic acid tert-butyl ester as a white solid (0.74 g, 47%), MS (ISP): 245.4 (M+H)$^{+}$.

Step 3. A suspension of sodium hydrogencarbonate (0.045 g,) in dimethoxyethane (1 mL) under argon was treated with 2-bromo-1-(4-chloro-phenyl)-ethanone (0.072 g, 0.29 mmol) and (R)-2-thiocarbamoyl-piperidine-1-carboxylic acid tert-butyl ester (0.050 g, 0.20 mmol). The mixture was stirred at room temperature for 24 h. After cooling to 0° C., pyridine (0.091 g, 0.093 mL) and trifluoroacetic anhydride (0.12 g, 0.077 mL) were added. The mixture was warmed back to room temperature and stirred for 0.5 h. The volatiles were evaporated and the residue dissolved in dichloromethane and washed with water and saturated sodium chloride. The organic phase was dried over sodium sulphate and evaporated. The residual yellow oil was (R)-2-[4-(4-chloro-phenyl)-thiazol-2-yl]-piperidine-1-carboxylic acid tert-butyl ester (0.080 g, 100%), which was used in the following step without purification.

Step 4. (R)-2-[4-(4-Chloro-phenyl)-thiazol-2-yl]-piperidine-1-carboxylic acid tert-butyl ester (0.077 g, 0.20 mmol) was dissolved in dichloromethane (1 mL) and treated with trifluoroacetic acid (1 mL). The mixture was stirred at room temperature for 30 min, then the volatiles were evaporated. The residual (R)-2-[4-(4-chloro-phenyl)-thiazol-2-yl]-piperidinium trifluoroacetate was used crude in the next step. In alternative, the residue was dissolved in dichloromethane and washed with saturated sodium hydrogencarbonate. The organic phase was dried over sodium sulphate and evaporated and the residual (R)-2-[4-(4-chloro-phenyl)-thiazol-2-yl]-piperidine used crude in the next step.

Step 5. A solution of (R)-2-[4-(4-chloro-phenyl)-thiazol-2-yl]-piperidinium trifluoroacetate (0.077 g, 0.20 mmol) in dry dichloromethane (2 mL) under argon was treated with triethylamine (0.079 g, 0.11 mL), dimethylaminopyridine (0.002 g, 0.020 mmol) and phenoxyacetyl chloride (0.033 g, 0.20 mmol). The mixture was stirred at room temperature for 16 h. The mixture was washed with water and saturated sodium chloride. The organic phase was dried over sodium sulphate and evaporated. The residual oil was purified by preparative HPLC: Column: YMC-Pack Pro C18 RS, 20×50 mm, S-5 um, 8 nm, No 200504707(W); Gradient: 0-0.4 min: 30% acetonitrile in (water+0.1% $HCO_2H$), 0.4-2 min: increse of acetonitrile fraction from 30% to 95%, 2.4-3.7 min: 95% acetonitrile, 3.7-3.8 min: decrease of acetonitrile fraction from 95% to 30%; Program end at 4 min; Flow: 30 ml/min. 1-{(R)-2-[4-(4-Chloro-phenyl)-thiazol-2-yl]-piperidin-1-yl}-2-phenoxy-ethanone was obtained after lyophilization as a light yellow oil (0.037 g, 46%), MS (ISP): 413.1, 415.4 $(M+H)^{+\cdot}$. $^1$H-NMR ($CDCl_3$, 300 MHz): 7.81 (2H, d), 7.38 (3H, m), 7.27 (2H, m), 6.98 (3H, m), 6.11+5.58 (1H, bs), 4.82 (2H, m), 4.56+3.91 (1H, bd), 3.36+2.86 (1H, bt), 2.59 (1H, m), 1.75 (5H, m).

Example 2

2-Phenoxy-1-[(R)-2-(4-phenyl-thiazol-2-yl)-piperidin-1-yl]-ethanone

2-Phenoxy-1-[(R)-2-(4-phenyl-thiazol-2-yl)-piperidin-1-yl]-ethanone, MS (ISP): 379.3 $(M+H)^+$, was prepared as illustrated in example 1, steps 1 to 5. Step 3 was performed with 2-bromo-1-phenyl-ethanone and yielded (R)-2-(4-phenyl-thiazol-2-yl)-piperidine-1-carboxylic acid tert-butyl ester, which was deprotected to (R)-2-(4-phenyl-thiazol-2-yl)-piperidine in step 4. This was converted to the title compound in step 5 (15.3 mg, 54%).

Example 3

4-{2-[(R)-1-(2-Phenoxy-acetyl)-piperidin-2-yl]-thiazol-4-yl}-benzoic acid

4-{2-[(R)-1-(2-Phenoxy-acetyl)-piperidin-2-yl]-thiazol-4-yl}-benzoic acid, MS (ISP): 423.3 $(M+H)^+$, was prepared as illustrated in example 1, steps 1 to 5. Step 3 was performed with 4-(2-bromo-acetyl)-benzoic acid and yielded (R)-2-[4-(4-carboxy-phenyl)-thiazol-2-yl]-piperidine-1-carboxylic acid tert-butyl ester, which was deprotected to 4-((R)-2-piperidin-2-yl-thiazol-4-yl)-benzoic acid in step 4. This was converted to the title compound in step 5 (8.9 mg, 27%).

Example 4

2-Phenoxy-1-{(R)-2-[4-(4-trifluoromethoxy-phenyl)-thiazol-2-yl]-piperidin-1-yl}-ethanone 2-Phenoxy-1-{(R)-2-[4-(4-trifluoromethoxy-phenyl)-thiazol-2-yl]-piperidin-1-yl}-ethanone, MS (ISP): 463.3 $(M+H)^+$, was prepared as illustrated in example 1, steps 1 to 5. Step 3 was performed with 2-bromo-1-(4-trifluoromethoxy-phenyl)-ethanone and yielded (R)-2-[4-(4-trifluoromethoxy-phenyl)-thiazol-2-yl]-piperidine-1-carboxylic acid tert-butyl ester, which was deprotected to (R)-2-[4-(4-trifluoromethoxy-phenyl)-thiazol-2-yl]-piperidine in step 4. This was converted to the title compound in step 5 (13.1 mg, 37%).

Example 5

3-{2-[(R)-1-(2-Phenoxy-acetyl)-piperidin-2-yl]-thiazol-4-yl}-benzoic acid

3-{2-[(R)-1-(2-Phenoxy-acetyl)-piperidin-2-yl]-thiazol-4-yl}-benzoic acid, MS (ISP): 421.1 (M–H), was prepared as illustrated in example 1, steps 1 to 5. Step 3 was performed with 3-(2-bromo-acetyl)-benzoic acid and yielded (R)-2-[4-(3-carboxy-phenyl)-thiazol-2-yl]-piperidine-1-carboxylic acid tert-butyl ester, which was deprotected to 3-((R)-2-piperidin-2-yl-thiazol-4-yl)-benzoic acid in step 4. This was converted to the title compound in step 5 (14.8 mg, 38%).

Example 6

2-Phenoxy-1-[(R)-2-(4-pyridin-2-yl-thiazol-2-yl)-piperidin-1-yl]-ethanone

2-Phenoxy-1-[(R)-2-(4-pyridin-2-yl-thiazol-2-yl)-piperidin-1-yl]-ethanone, MS (ISP): 380.3 $(M+H)^{+\cdot}$, was prepared as illustrated in example 1, steps 1 to 5. Step 3 was performed with 2-bromo-1-pyridin-2-yl-ethanone and yielded (R)-2-(4-pyridin-2-yl-thiazol-2-yl)-piperidine-1-carboxylic acid tert-butyl ester, which was deprotected to 2-((R)-2-piperidin-2-yl-thiazol-4-yl)-pyridine in step 4. This was converted to the title compound in step 5 (10.5 mg, 31%).

Example 7

1-{(R)-2-[4-(3,4-Difluoro-phenyl)-thiazol-2-yl]-piperidin-1-yl}-2-phenoxy-ethanone 1-{(R)-2-[4-(3,4-Difluoro-phenyl)-thiazol-2-yl]-piperidin-1-yl}-2-phenoxy-ethanone, MS (ISP): 415.2 $(M+H)^+$, was prepared as illustrated in example 1, steps 1 to 5. Step 3 was performed with 2-bromo-1-(3,4-difluoro-phenyl)-ethanone and yielded (R)-2-[4-(3,4-difluoro-phenyl)-thiazol-2-yl]-piperidine-1-carboxylic acid tert-butyl ester, which was deprotected to (R)-2-[4-(3,4-difluoro-phenyl)-thiazol-2-yl]-piperidine in step 4. This was converted to the title compound in step 5 (14.1 mg, 53%).

Example 8

2-Phenoxy-1-[(R)-2-(4-pyridin-3-yl-thiazol-2-yl)-piperidin-1-yl]-ethanone

2-Phenoxy-1-[(R)-2-(4-pyridin-3-yl-thiazol-2-yl)-piperidin-1-yl]-ethanone, MS (ISP): 380.2 $(M+H)^+$, was prepared as illustrated in example 1, steps 1 to 5. Step 3 was performed with 2-bromo-1-pyridin-3-yl-ethanone and yielded (R)-2-(4-pyridin-3-yl-thiazol-2-yl)-piperidine-1-carboxylic acid tert-butyl ester, which was deprotected to 3-((R)-2-piperidin-2-yl-thiazol-4-yl)-pyridine in step 4. This was converted to the title compound in step 5 (8.1 mg, 22%).

Example 9

1-{(R)-2-[4-(5-Chloro-2-methoxy-phenyl)-thiazol-2-yl]-piperidin-1-yl}-2-phenoxy-ethanone 1-{(R)-2-[4-(5-Chloro-2-methoxy-phenyl)-thiazol-2-yl]-piperidin-1-yl}-2-phenoxy-ethanone, MS (ISP): 443.2 $(M+H)^+$, was prepared as illustrated in example 1, steps 1 to 5. Step 3 was performed with 2-bromo-1-(5-chloro-2-methoxy-phenyl)-ethanone and yielded (R)-2-[4-(5-chloro-2-methoxy-phenyl)-thiazol-2-yl]-piperidine-1-carboxylic acid tert-butyl ester) which was deprotected to (R)-2-[4-(5-chloro-2-methoxy-phenyl)-thiazol-2-yl]-piperidine in step 4. This was converted to the title compound in step 5 (20.1 mg, 49%).

Example 10

2-Phenoxy-1-[(R)-2-(4-pyridin-4-yl-thiazol-2-yl)-piperidin-1-yl]-ethanone

2-Phenoxy-1-[(R)-2-(4-pyridin-4-yl-thiazol-2-yl)-piperidin-1-yl]-ethanone, MS (ISP): 380.2 $(M+H)^+$, was prepared as illustrated in example 1, steps 1 to 5. Step 3 was performed with 2-bromo-1-pyridin-4-yl-ethanone and yielded (R)-2-(4-pyridin-4-yl-thiazol-2-yl)-piperidine-1-carboxylic acid tert-butyl ester, which was deprotected to 4-((R)-2-piperidin-2-yl-thiazol-4-yl)-pyridine in step 4. This was converted to the title compound in step 5 (6.9 mg 23%).

Example 11

1-{(R)-2-[4-(2-Methoxy-phenyl)-thiazol-2-yl]-piperidin-1-yl}-2-phenoxy-ethanone

1-{(R)-2-[4-(2-Methoxy-phenyl)-thiazol-2-yl]-piperidin-1-yl}-2-phenoxy-ethanone, MS (ISP): 409.3 $(M+H)^+$, was prepared as illustrated in example 1, steps 1 to 5. Step 3 was performed with 2-bromo-1-(2-methoxy-phenyl)-ethanone and yielded (R)-2-[4-(2-methoxy-phenyl)-thiazol-2-yl]-piperidine-1-carboxylic acid tert-butyl ester, which was deprotected to (R)-2-[4-(2-methoxy-phenyl)-thiazol-2-yl]-piperidine in step 4. This was converted to the title compound in step 5 (15.4 mg, 44%).

Example 12

1-{(R)-2-[4-(4-Methanesulfonyl-phenyl)-thiazol-2-yl]-piperidin-1-yl}-2-phenoxy-ethanone 1-{(R)-2-[4-(4-Methanesulfonyl-phenyl)-thiazol-2-yl]-piperidin-1-yl}-2-phenoxy-ethanone, MS (ISP): 457.3 $(M+H)^+$, was prepared as illustrated in example 1, steps 1 to 5. Step 3 was performed with 2-bromo-1-(4-methanesulfonyl-phenyl)-ethanone and yielded (R)-2-[4-(4-methanesulfonyl-phenyl)-thiazol-2-yl]-piperidine-1-carboxylic acid tert-butyl ester, which was deprotected to (R)-2-[4-(4-methanesulfonyl-phenyl)-thiazol-2-yl]-piperidine in step 4. This was converted to the title compound in step 5 (10.4 mg, 23%).

Example 13

6-{2-[(R)-1-(2-Phenoxy-acetyl)-piperidin-2-yl]-thiazol-4-yl}-pyridine-2-carboxylic acid methyl ester 6-{2-[(R)-1-(2-Phenoxy-acetyl)-piperidin-2-yl]-thiazol-4-yl}-pyridine-2-carboxylic acid methyl ester, MS (ISP): 438.3 $(M+H)^+$, was prepared as illustrated in example 1, steps 1 to 5. Step 3 was performed with 2 6-(2-bromo-acetyl)-pyridine-2-carboxylic acid methyl ester and yielded 6-[2-((R)-1-tert-butoxycarbonyl-piperidin-2-yl)-thiazol-4-yl]-pyridine-2-carboxylic acid methyl ester, which was deprotected to 6-((R)-2-piperidin-2-yl-thiazol-4-yl)-pyridine-2-carboxylic acid methyl ester in step 4. This was converted to the title compound in step 5 (8.9 mg, 21%).

Example 14

5-{2-[(R)-1-(2-Phenoxy-acetyl)-piperidin-2-yl]-thiazol-4-yl}-1,3-dihydro-indol-2-one 5-{2-[(R)-1-(2-Phenoxy-acetyl)-piperidin-2-yl]-thiazol-4-yl}-1,3-dihydro-indol-2-one MS (ISP): 434.3 $(M+H)^+$, was prepared as illustrated in example 1, steps 1 to 5. Step 3 was performed with 5-(2-bromo-acetyl)-1,3-dihydro-indol-2-one and yielded (R)-2-[4-(2-oxo-2,3-dihydro-1H-indol-5-yl)-thiazol-2-yl]-piperidine-1-carboxylic acid tert-butyl ester, which was deprotected to 5-((R)-2-piperidin-2-yl-thiazol-4-yl)-1,3-dihydro-indol-2-one in step 4. This was converted to the title compound in step 5 (2.8 mg, 6%).

Example 15

N-(4-{2-[(R)-1-(2-Phenoxy-acetyl)-piperidin-2-yl]-thiazol-4-yl}-phenyl)-acetamide N-(4-{2-[(R)-1-(2-Phenoxy-acetyl)-piperidin-2-yl]-thiazol-4-yl}-phenyl)-acetamide, MS (ISP): 436.3 $(M+H)^+$, was prepared as illustrated in example 1, steps 1 to 5. Step 3 was performed with N-[4-(2-bromo-acetyl)-phenyl]-acetamide and yielded (R)-2-[4-(4-acetylamino-phenyl)-thiazol-2-yl]-piperidine-1-carboxylic acid tert-butyl ester, which was deprotected to N-[4-((R)-2-piperidin-2-yl-thiazol-4-yl)-phenyl]-acetamide in step 4. This was converted to the title compound in step 5 (3.1 mg, 7%).

Example 16

1-{(R)-2-[4-(4-Hydroxy-phenyl)-thiazol-2-yl]-piperidin-1-yl}-2-phenoxy-ethanone

1-{(R)-2-[4-(4-Hydroxy-phenyl)-thiazol-2-yl]-piperidin-1-yl}-2-phenoxy-ethanone, MS (ISP): 395.2 $(M+H)^+$, was prepared as illustrated in example 1, steps 1 to 5. Step 3 was performed with 2-bromo-1-(4-hydroxy-phenyl)-ethanone and yielded (R)-2-[4-(4-hydroxy-phenyl)-thiazol-2-yl]-piperidine-1-carboxylic acid tert-butyl ester, which was deprotected to 4-((R)-2-piperidin-2-yl-thiazol-4-yl)-phenol in step 4. This was converted to the tide compound in step 5 (2.5 mg, 6%).

Example 17

1-[(R)-2-(4-Benzo[1,3]dioxol-5-yl-thiazol-2-yl)-piperidin-1-yl]-2-phenoxy-ethanone 1-[(R)-2-(4-Benzo[1,3]dioxol-5-yl-thiazol-2-yl)-piperidin-1-yl]-2-phenoxy-ethanone, MS (ISP): 423.3 $(M+H)^+$, was prepared as illustrated in example 1, steps 1 to 5. Step 3 was performed with 1-benzo[1,3]dioxol-5-yl-2-bromo-ethanone and yielded (R)-2-(4-benzo[1,3]dioxol-5-yl-thiazol-2-yl)-piperidine-1-carboxylic acid tert-butyl ester, which was deprotected to (R)-2-(4-benzo[1,3]dioxol-5-yl-thiazol-2-yl)-piperidine in step 4. This was converted to the title compound in step 5 (9.6 mg, 23%).

Example 18

1-{(R)-2-[4-(4-Dimethylamino-phenyl)-thiazol-2-yl]-piperidin-1-yl}-2-phenoxy-ethanone 1-{(R)-2-[4-(4-Dimethylamino-phenyl)-thiazol-2-yl]-piperidin-1-yl}-2-phenoxy-ethanone, MS (ISP): 422.3 (M+H)+, was prepared as illustrated in example 1, steps 1 to 5. Step 3 was performed with 2-bromo-1-(4-dimethylamino-phenyl)-ethanone and yielded (R)-2-[4-(4-dimethylamino-phenyl)-thiazol-2-yl]-piperidine-1-carboxylic acid tert-butyl ester, which was deprotected to dimethyl-[4-((R)-2-piperidin-2-yl-thiazol-4-yl)-phenyl]-amine in step 4. This was converted to the title compound in step 5 (10.6 mg, 25%).

Example 19

1-{(R)-2-[4-(3-Methyl-1H-indol-2-yl)-thiazol-2-yl]-piperidin-1-yl}-2-phenoxy-ethanone 1-{(R)-2-[4-(3-Methyl-1H-indol-2-yl)-thiazol-2-yl]-piperidin-1-yl}-2-phenoxy-ethanone, MS (ISP): 432.6 (M+H)+, was prepared as illustrated in example 1, steps 1 to 5. Step 3 was performed with 2-bromo-1-(3-methyl-1H-indol-2-yl)-ethanone and yielded (R)-2-[4-(3-methyl-1H-indol-2-yl)-thiazol-2-yl]-piperidine-1-carboxylic acid tert-butyl ester, which was deprotected to 3-methyl-2-((R)-2-piperidin-2-yl-thiazol-4-yl)-1H-indole in step 4. This was converted to the title compound in step 5 (5.2 mg, 12%).

Example 20

4-{2-[(R)-1-(2-Phenoxy-acetyl)-piperidin-2-yl]-thiazol-4-yl}-benzonitrile

4-{2-[(R)-1-(2-Phenoxy-acetyl)-piperidin-2-yl]-thiazol-4-yl}-benzonitrile, MS (ISP): 404.2 (M+H)+, was prepared as illustrated in example 1, steps 1 to 5. Step 3 was performed with 4-(2-bromo-acetyl)-benzonitrile and yielded (R)-2-[4-(4-cyano-phenyl)-thiazol-2-yl]-piperidine-1-carboxylic acid tert-butyl ester, which was deprotected to 4-((R)-2-piperidin-2-yl-thiazol-4-yl)-benzonitrile in step 4. This was converted to the title compound in step 5 (6.3 mg, 16%).

Example 21

3-{2-[(R)-1-(2-Phenoxy-acetyl)-piperidin-2-yl]-thiazol-4-yl}-benzonitrile

3-{2-[(R)-1-(2-Phenoxy-acetyl)-piperidin-2-yl]-thiazol-4-yl}-benzonitrile, MS (ISP): 404.2 (M+H)+, was prepared as illustrated in example 1, steps 1 to 5. Step 3 was performed with 3-(2-bromo-acetyl)-benzonitrile and yielded (R)-2-[4-(3-cyano-phenyl)-thiazol-2-yl]-piperidine-1-carboxylic acid tert-butyl ester, which was deprotected to 3-((R)-2-piperidin-2-yl-thiazol-4-yl)-benzonitrile in step 4. This was converted to the title compound in step 5 (5.8 mg, 14%).

Example 22

1-{(R)-2-[4-(6-Chloro-pyridin-3-yl)-thiazol-2-yl]-piperidin-1-yl}-2-phenoxy-ethanone 1-{(R)-2-[4-(6-Chloro-pyridin-3-yl)-thiazol-2-yl]-piperidin-1-yl}-2-phenoxy-ethanone, MS (ISP): 414.1 (M+H)+, was prepared as illustrated in example 1, steps 1 to 5. Step 3 was performed with 2-bromo-1-(6-chloro-pyridin-3-yl)-ethanone and yielded (R)-2-[4-(6-chloro-pyridin-3-yl)-thiazol-2-yl]-piperidine-1-carboxylic acid tert-butyl ester, which was deprotected to 2-chloro-5-((R)-2-piperidin-2-yl-thiazol-4-yl)-pyridine in step 4. This was converted to the title compound in step 5 (4.9 mg, 12%).

Example 23

1-{((R)-2-[4-(5-Bromo-thiophen-2-yl)-thiazol-2-yl]-piperidin-1-yl}-2-phenoxy-ethanone 1-{(R)-2-[4-(5-Bromo-thiophen-2-yl)-thiazol-2-yl]-piperidin-1-yl}-2-phenoxy-ethanone, MS (ISP): 463.1, 465.1 (M+H)+, was prepared as illustrated in example 1, steps 1 to 5. Step 3 was performed with 2-bromo-1-(5-bromo-thiophen-2-yl)-ethanone and yielded (R)-2-[4-(5-bromo-thiophen-2-yl)-thiazol-2-yl]-piperidine-1-carboxylic acid tert-butyl ester, which was deprotected to (R)-2-[4-(5-bromo-thiophen-2-yl)-thiazol-2-yl]-piperidine in step 4. This was converted to the title compound in step 5 (10.5 mg, 23%).

Example 24

3-{4-[(R)-1-(2-Phenoxy-acetyl)-piperidin-2-yl]-thiazol-2-yl}-benzoic acid methyl ester The title compound was prepared as illustrated in scheme 2, steps 1 to 5.

Step 1. A solution of (R)-(+)-piperidine-1,2-dicarboxylic acid 1-tert-butyl ester (1.00 g, 4.4 mmol) in dry tetrahydrofuran (9.6 mL) was cooled to 0° C. and treated with diisopropylethylamine (0.95 g, 1.3 mL) and isobutyl chloroformate (0.89 g, 0.86 mL, 6.5 mmol). A white suspension formed, which was stirred at 0° C. for 4 h. The mixture was then diluted with acetonitrile (6.6 mL) until a clear solution was obtained. A cooled (0° C.) solution of trimethylsilyl diazomethane (2N in hexanes, 4.4 mL, 8.7 mmol) in dry tetrahydrofuran (3 mL) and acetonitrile (3 mL) was added to the reaction mixture during 3 min. The mixture was then stirred at 0° C. for 3 h, and at room temperature for 16 h. The volatiles were evaporated and the residue purified by flash chromatography (heptane/ethyl acetate gradient) to yield 2-(2-diazo-acetyl)-piperidine-1-carboxylic acid tert-butyl ester as a yellow oil (0.26 g, 23%), MS (ISP): 254.14 (M+H)+.

Step 2. A solution of 2-(2-diazo-acetyl)-piperidine-1-carboxylic acid tert-butyl ester (0.51 g, 2.0 mmol) in dry ethyl acetate (11 mL) was cooled to −45° C. and treated with a 33% solution of hydrobromic acid in acetic acid (0.24 mL), which was added dropwise over 45 min. The cold reaction mixture was diluted with tert-butyl methyl ether (34 mL) and left to warm to room temperature. The mixture was washed twice with saturated sodium hydrogenocarbonate (2*11 mL) and with saturated sodium chloride. The organic phase was dried over sodium sulphate and evaporated. The residue was purified by flash chromatography (heptane/ethyl acetate gradient) to yield 2-(2-bromo-acetyl)-piperidine-1-carboxylic acid tert-butyl ester (0.28 g, 45%) as a light yellow oil, MS (ISP): 306.1, 308.1 (M+H)+.

Step 3. A suspension of sodium hydrogencarbonate (0.042 g) in dimethoxyetane (0.5 mL) under argon was treated with a solution of 2-(2-bromacetyl)-piperidine-1-carboxylic acid tert-butyl ester (0.085 g, 0.28 mmol) in dimethoxyethane (0.5 mL). 3-Thiocarbamoyl-benzoic acid methyl ester (0.036 g, 0.18 mmol) was added and the mixture was stirred at room temperature for 24 h. After cooling to 0° C., pyridine (0.082 g, 0.084 mL) and trifluoroacetic anhydride (0.10 g, 0.070 mL) were added. The mixture was left to warm to room temperature and stirred for 1 h. The volatiles were evaporated and the residue was dissolved in ethyl acetate and washed with water and saturated sodium chloride. The organic phase was dried over sodium sulphate and evaporated. The residual (R)-2-[2-(3-methoxycarbonyl-phenyl)-thiazol-4-yl]-piperidine-1-carboxylic acid tert-butyl ester (0.060 g, 81%), MS (ISP): 403.4 $(M+H)^{+\cdot}$, was used without further purification.

Step 4. (R)-2-[2-(3-Methoxycarbonyl-phenyl)-thiazol-4-yl]-piperidine-1-carboxylic acid tert-butyl ester (0.060 g, 0.15 mmol) was dissolved in dichloromethane (1 mL) and treated with trifluoroacetic acid (1 mL). The mixture was stirred at room temperature for 50 min, then the volatiles were evaporated. The residue was dissolved in dichloromethane and washed with saturated sodium hydrogencarbonate. The organic phase was dried over sodium sulphate and evaporated and the residual 3-((R)-4-piperidin-2-yl-thiazol-2-yl)-benzoic acid methyl ester was used crude in the next step.

Step 5. A solution of 3-((R)-4-piperidin-2-yl-thiazol-2-yl)-benzoic acid methyl ester (0.048 g, 0.16 mmol) in dry dichloromethane (2 mL) under argon was treated with triethylamine (0.064 g, 0.09 ml.), dimethylaminopyridine (0.002 g, 0.020 mmol) and phenoxyacetyl chloride (0.027 g, 0.16 mmol). The mixture was stirred at room temperature for 4 h. The mixture was washed with water and saturated sodium chloride. The organic phase was dried over sodium sulphate and evaporated. The residual oil was purified by preparative HPLC: Column: YMC-Pack Pro C18 RS, 20×50 mm, S-5 um, 8 nm, No200504707(W); Gradient: 0-0.4 min: 30% acetonitrile in (water+0.1% HCO$_2$H), 0.4-2.4 min: increse of acetonitrile fraction from 30% to 95%, 2.4-4.7 min: 95% acetonitrile, 4.7-4.8 min: decrease of acetonitrile fraction from 95% to 30%; Program end at 4.87 min; Flow: 30 ml/min. 3-{4-[(R)-1-(2-Phenoxy-acetyl)-piperidin-2-yl]-thiazol-2-yl}-benzoic acid methyl ester was obtained after lyophilization as a light yellow oil (0.033 g, 48%), MS (ISP): 437.3 $(M+H)^{+\cdot}$.

Example 25

N-(4-{4-[(R)-1-(2-Phenoxy-acetyl)-piperidin-2-yl]-thiazol-2-yl}-phenyl)-acetamide N-(4-{4-[(R)-1-(2-Phenoxy-acetyl)-piperidin-2-yl]-thiazol-2-yl}-phenyl)-acetamide, MS (ISP): 436.2 $(M+H)^{+\cdot}$, was prepared as illustrated in example 24, steps 1 to 5. Step 3 was performed with N-(4-thiocarbamoyl-phenyl)-acetamide and yielded (R)-2-[2-(4-acetylamino-phenyl)-thiazol-4-yl]-piperidine-1-carboxylic acid tert-butyl ester, which was deprotected to N-[4-((R)-4-piperidin-2-yl-thiazol-2-yl)-phenyl]-acetamide in step 4. This was converted to the title compound in step 5 (10.2 mg, 42%).

Example 26

1-{(R)-2-[2-(1H-Indazol-3-yl)-thiazol-4-yl]-piperidin-1-yl}-2-phenoxy-ethanone

1-{(R)-2-[2-(1H-Indazol-3-yl)-thiazol-4-yl]-piperidin-1-yl}-2-phenoxy-ethanone, MS (ISP): 419.0 $(M+H)^+$, was prepared as illustrated in example 24, steps 1 to 5. Step 3 was performed with 1H-indazole-3-carbothioic acid amide and yielded (R)-2-[2-(1H-indazol-3-yl)-thiazol-4-yl]-piperidine-1-carboxylic acid tert-butyl ester, which was deprotected to 3-((R)-4-piperidin-2-yl-thiazol-2-yl)-1H-indazole in step 4. This was converted to the title compound in step 5 (9.1 mg, 31%).

Example 27

2-Phenoxy-1-{(R)-2-[2-(6-trifluoromethyl-pyridin-3-yl)-thiazol-4-yl]-piperidin-1-yl}-ethanone 2-Phenoxy-1-{(R)-2-[2-(6-trifluoromethyl-pyridin-3-yl)-thiazol-4-yl]-piperidin-1-yl}-ethanone, MS (ISP): 448.0 $(M+H)^+$, was prepared as illustrated in example 24, steps 1 to 5. Step 3 was performed with 6-trifluoromethyl-thionicotinamide and yielded (R)-2-[2-(6-trifluoromethyl-pyridin-3-yl)-thiazol-4-yl]-piperidine-1-carboxylic acid tert-butyl ester, which was deprotected to 5-((R)-4-piperidin-2-yl-thiazol-2-yl)-2-trifluoromethyl-pyridine in step 4. This was converted to the title compound in step 5 (9.5 mg, 34%).

Example 28

2-Phenoxy-1-{(R)-2-[2-(5-trifluoromethyl-pyridin-2-yl)-thiazol-4-yl]-piperidin-1-yl}-ethanone 2-Phenoxy-1-{(R)-2-[2-(5-trifluoromethyl-pyridin-2-yl)-thiazol-4-yl]-piperidin-1-yl}-ethanone, MS (ISP): 448.0 $(M+H)^+$, was prepared as illustrated in example 24, steps 1 to 5. Step 3 was performed with 5-trifluoromethyl-pyridine-2-carbothioic acid amide and yielded (R)-2-[2-(5-trifluoromethyl-pyridin-2-yl)-thiazol-4-yl]-piperidine-1-carboxylic acid tert-butyl ester, which was deprotected to 2-((R)-4-piperidin-2-yl-thiazol-2-yl)-5-trifluoromethyl-pyridine in step 4. This was converted to the title compound in step 5 (10.4 mg, 27%).

Example 29

2-Phenoxy-1-[(R)-2-(2-pyrazin-2-yl-thiazol-4-yl)-piperidin-1-yl]-ethanone

2-Phenoxy-1-[(R)-2-(2-pyrazin-2-yl-thiazol-4-yl)-piperidin-1-yl]-ethanone, MS (ISP): 381.1 $(M+H)^+$, was prepared as illustrated in example 24, steps 1 to 5. Step 3 was performed with pyrazine-2-carbothioic acid amide and yielded (R)-2-(2-pyrazin-2-yl-thiazol-4-yl)-piperidine-1-carboxylic acid tert-butyl ester, which was deprotected to 2-((R)-4-piperidin-2-yl-thiazol-2-yl)-pyrazine in step 4. This was converted to the title compound in step 5 (1.9 mg, 10%).

Example 30

1-{(R)-2-[2-(6-Methyl-pyridin-3-yl)-thiazol-4-yl]-piperidin-1-yl}-2-phenoxy-ethanone 1-{(R)-2-[2-(6-Methyl-pyridin-3-yl)-thiazol-4-yl]-piperidin-1-yl}-2-phenoxy-ethanone, MS (ISP): 394.0 $(M+H)^+$, was prepared as illustrated in example 24, steps 1 to 5. Step 3 was performed with 6-methyl-thionicotinamide and yielded (R)-2-[2-(6-methyl-pyridin-3-yl)-thiazol-4-yl]-piperidine-1-carboxylic acid tert-butyl ester, which was deprotected to 2-methyl-5-((R)-4-piperidin-2-yl-thiazol-2-yl)-pyridine in step 4. This was converted to the title compound in step 5 (5.4 mg, 28%).

Example 31

2-Phenoxy-1-[(R)-2-(2-pyridin-3-yl-thiazol-4-yl)-piperidin-1-yl]-ethanone

2-Phenoxy-1-[(R)-2-(2-pyridin-3-yl-thiazol-4-yl)-piperidin-1-yl]-ethanone, MS (ISP): 380.1 (M+H)$^+$, was prepared as illustrated in example 24, steps 1 to 5. Step 3 was performed with thionicotinamide and yielded (R)-2-(2-pyridin-3-yl-thiazol-4-yl)-piperidine-1-carboxylic acid tert-butyl ester, which was deprotected to 3-((R)-4-piperidin-2-yl-thiazol-2-yl)-pyridine in step 4. This was converted to the title compound in step 5 (3.2 mg, 29%).

Example 32

2-Phenoxy-1-[(R)-2-(2-pyridin-4-yl-thiazol-4-yl)-piperidin-1-yl]-ethanone

2-Phenoxy-1-[(R)-2-(2-pyridin-4-yl-thiazol-4-yl)-piperidin-1-yl]-ethanone, MS (ISP): 380.1 (M+H)$^+$, was prepared as illustrated in example 24, steps 1 to 5. Step 3 was performed with thioisonicotinamide and yielded (R)-2-(2-pyridin-4-yl-thiazol-4-yl)-piperidine-1-carboxylic acid tert-butyl ester, which was deprotected to 4-((R)-4-piperidin-2-yl-thiazol-2-yl)-pyridine in step 4. This was converted to the title compound in step 5 (2.3 mg, 16%).

Example 33

1-{(R)-2-[2-(6-Methoxy-pyridin-3-yl)-thiazol-4-yl]-piperidin-1-yl}-2-phenoxy-ethanone 1-{(R)-2-[2-(6-Methoxy-pyridin-3-yl)-thiazol-4-yl]-piperidin-1-yl}-2-phenoxy-ethanone, MS (ISP): 410.3 (M+H)$^+$, was prepared as illustrated in example 24, steps 1 to 5. Step 3 was performed with 6-methoxy-thionicotinamide and yielded (R)-2-[2-(6-methoxy-pyridin-3-yl)-thiazol-4-yl]-piperidine-1-carboxylic acid tert-butyl ester, which was deprotected to 2-methoxy-5-((R)-4-piperidin-2-yl-thiazol-2-yl)-pyridine in step 4. This was converted to the title compound in step 5 (18.4 mg, 56%).

Example 34

2-Phenoxy-1-[(R)-2-(2-pyridin-2-yl-thiazol-4-yl)-piperidin-1-yl]-ethanone

2-Phenoxy-1-[(R)-2-(2-pyridin-2-yl-thiazol-4-yl)-piperidin-1-yl]-ethanone, MS (ISP): 380.1 (M+H)$^+$, was prepared as illustrated in example 24, steps 1 to 5. Step 3 was performed with pyridine-2-carbothioic acid amide and yielded (R)-2-(2-pyridin-2-yl-thiazol-4-yl)-piperidine-1-carboxylic acid tert-butyl ester, which was deprotected to 2-((R)-4-piperidin-2-yl-thiazol-2-yl)-pyridine in step 4. This was converted to the title compound in step 5 (7.8 mg, 31%).

Example 35

1-{(R)-2-[2-(4-Fluoro-phenyl)-thiazol-4-yl]-piperidin-1-yl}-2-phenoxy-ethanone

1-{(R)-2-[2-(4-Fluoro-phenyl)-thiazol-4-yl]-piperidin-1-yl}-2-phenoxy-ethanone, MS (ISP): 397.0 (M+H)$^+$, was prepared as illustrated in example 24, steps 1 to 5. Step 3 was performed with 4-fluoro-thiobenzamide and yielded (R)-2-[2-(4-fluoro-phenyl)-thiazol-4-yl]-piperidine-1-carboxylic acid tert-butyl ester, which was deprotected (R)-2-[2-(4-fluoro-phenyl)-thiazol-4-yl]-piperidine in step 4. This was converted to the title compound in step 5 (19.6 mg, 55%).

Example 36

4-{4-[(R)-1-(2-Phenoxy-acetyl)-piperidin-2-yl]-thiazol-2-yl}-benzoic acid methyl ester 4-{4-[(R)-1-(2-Phenoxy-acetyl)-piperidin-2-yl]-thiazol-2-yl}-benzoic acid methyl ester, MS (ISP): 437.2 (M+H)$^+$, was prepared as illustrated in example 24, steps 1 to 5. Step 3 was performed with 4-thiocarbamoyl-benzoic acid methyl ester and yielded (R)-2-[2-(4-methoxycarbonyl-phenyl)-thiazol-4-yl]-piperidine-1-carboxylic acid tert-butyl ester, which was deprotected 4-((R)-4-piperidin-2-yl-thiazol-2-yl)-benzoic acid methyl ester in step 4. This was converted to the title compound in step 5 (42.3 mg, 54%).

Example 37

1-{(R)-2-[2-(4-Chloro-benzyl)-thiazol-4-yl]-piperidin-1-yl}-2-phenoxy-ethanone

1-{(R)-2-[2-(4-Chloro-benzyl)-thiazol-4-yl]-piperidin-1-yl}-2-phenoxy-ethanone, MS (ISP): 427.1 (M+H)$^+$, was prepared as illustrated in example 24, steps 1 to 5. Step 3 was performed with 2-(4-chloro-phenyl)-thioacetamide and yielded (R)-2-[2-(4-chloro-benzyl)-thiazol-4-yl]-piperidine-1-carboxylic acid tert-butyl ester, which was deprotected (R)-2-[2-(4-chloro-benzyl)-thiazol-4-yl]-piperidine in step 4. This was converted to the title compound in step 5 (19.7 mg, 52%).

Example 38

1-{(R)-2-[2-(2,3-Dihydro-benzo[1,4]dioxin-2-yl)-thiazol-4-yl]-piperidin-1-yl}-2-phenoxy-ethanone 1-{(R)-2-[2-(2,3-Dihydro-benzo[1,4]dioxin-2-yl)-thiazol-4-yl]-piperidin-1-yl}-2-phenoxy-ethanone, MS (ISP): 437.2 (M+H)$^+$, was prepared as illustrated in example 24, steps 1 to 5. Step 3 was performed with 2,3-dihydro-benzo[1,4]dioxine-2-carbothioic acid amide and yielded (R)-2-[2-(2,3-dihydro-benzo[1,4]dioxin-2-yl)-thiazol-4-yl]-piperidine-1-carboxylic acid tert-butyl ester, which was deprotected (R)-2-[2-(2,3-dihydro-benzo[1,4]dioxin-2-yl)-thiazol-4-yl]-piperidine in step 4. This was converted to the title compound in step 5 (10.1 mg, 26%).

Example 39

4-{2-[(R)-1-(2-Phenoxy-acetyl)-piperidin-2-yl]-thiazol-4-yl}-benzamide

4-{2-[(R)-1-(2-Phenoxy-acetyl)-piperidin-2-yl]-thiazol-4-yl}-benzamide, MS (ISP): 422.4 (M+H)$^+$, was prepared as illustrated in example 24, steps 1 to 5. Step 3 was performed with 4-thiocarbamoyl-benzamide and yielded (R)-2-[2-(4-carbamoyl-phenyl)-thiazol-4-yl]-piperidine-1-carboxylic acid tert-butyl ester, which was deprotected to 4-((R)-4-piperidin-2-yl-thiazol-2-yl)-benzamide in step 4. This was converted to the title compound in step 5 (6.7 mg, 14%).

Example 40

3-{4-[(R)-1-(2-Phenoxy-acetyl)-piperidin-2-yl]-thiazol-2-yl}-benzoic acid

A solution of 3-{4-[(R)-1-(2-phenoxy-acetyl)-piperidin-2-yl]-thiazol-2-yl}-benzoic acid methyl ester (0.030 g, 0.069 mmol) (prepared as illustrated in example 24) in methanol (0.5 mL) was treated with 1N KOH (0.14 mL, 0.14 mmol). The mixture was stirred at room temperature for 16 h, then diluted with water (0.5 mL) and acidified to pH 1 with HCl 0.5N. A white solid precipitated, which was filtered to yield 3-{4-[(R)-1-(2-phenoxy-acetyl)-piperidin-2-yl]-thiazol-2-yl}-benzoic acid (0.022 g, 76%), MS (ISP): 421.3 (M−H). $^1$H-NMR (CDCl$_3$, 300 MHz): 13.33 (1H, bs), 8.44 (1H, s), 8.15 (1H, d), 8.04 (1H, d), 7.65 (1H, m), 7.23 (2H, m), 6.92 (3H, m), 5.76+5.33 (1H, bs), 4.94 (2H, m), 4.34+3.80 (1H, bd), 3.32 (3H, m), 1.64 (4H, m).

Example 41

4-{4-[(R)-1-(2-Phenoxy-acetyl)-piperidin-2-yl]-thiazol-2-yl}-benzoic acid

4-{4-[(R)-1-(2-Phenoxy-acetyl)-piperidin-2-yl]-thiazol-2-yl}-benzoic acid, MS (ISP): 420.9 (M−H), was prepared as illustrated in example 40, using 4-{4-[(R)-1-(2-phenoxy-acetyl)-piperidin-2-yl]-thiazol-2-yl}-benzoic acid methly ester (prepared as illustrated in example 36) as starting material.

Example 42

6-{2-[(R)-1-(2-Phenoxy-acetyl)-piperidin-2-yl]-thiazol-4-yl}-pyridine-2-carboxylic acid 6-{2-[(R)-1-(2-Phenoxy-acetyl)-piperidin-2-yl]-thiazol-4-yl}-pyridine-2-carboxylic acid, MS (ISP): 424.3 (M+H)$^+$, was prepared as illustrated in example 40, using 6-{2-[(R)-1-(2-phenoxy-acetyl)-piperidin-2-yl]-thiazol-4-yl}-pyridine-2-carboxylic acid methly ester (prepared as illustrated in example 13) as starting material.

Example 43

Sodium; 4-{2-[(R)-1-(2-phenoxy-acetyl)-piperidin-2-yl]-thiazol-4-yl}-benzoate 4-{2-[(R)-1-(2-Phenoxy-acetyl)-piperidin-2-yl]-thiazol-4-yl}-benzoic acid (prepared as illustrated in example 3) (0.078 g, 0.18 mmol) was treated with a 0.25N solution of sodium methoxide in methanol until pH was neutral. The mixture was diluted with ether and the precipitate was filtered washing with ether, to yield sodium; 4-{2-[(R)-1-(2-phenoxy-acetyl)-piperidin-2-yl]-thiazol-4-yl}-benzoate as a white solid (0.077 g, 94%), MS (ISP): 421.1 (M−H).

Example 44

Sodium; 3-{2-[(R)-1-(2-phenoxy-acetyl)-piperidin-2-yl]-thiazol-4-yl}-benzoate Sodium; 3-{2-[(R)-1-(2-phenoxy-acetyl)-piperidin-2-yl]-thiazol-4-yl}-benzoate, MS (ISP): 421.1 (M−H), was prepared as illustrated for example 43, starting from 3-{2-[(R)-1-(2-Phenoxy-acetyl)-piperidin-2-yl]-thiazol-4-yl}-benzoic acid (prepared as illustrated in example 5).

Example 45

3-{5-Methyl-2-[(R)-1-(2-phenoxy-acetyl)-piperidin-2-yl]-thiazol-4-yl}-benzoic acid methyl ester 3-{5-Methyl-2-[(R)-1-(2-phenoxy-acetyl)-piperidin-2-yl]-thiazol-4-yl}-benzoic acid methyl ester, MS (ISP): 451.1 (M+H)$^+$, was prepared as illustrated in example 1, steps 1 to 5. Step 3 was performed with 3-(2-bromo-propionyl)-benzoic acid methyl ester and yielded (R)-2-[4-(3-methoxycarbonyl-phenyl)-5-methyl-thiazol-2-yl]-piperidine-1-carboxylic acid tert-butyl ester, which was deprotected to 3-((R)-5-methyl-2-piperidin-2-yl-thiazol-4-yl)-benzoic acid methyl ester in step 4. This was converted to the title compound in step 5 (49 mg, 48%).

3-(2-Bromo-propionyl)-benzoic acid methyl ester was prepared as illustrated in the scheme below, step 1 to 3

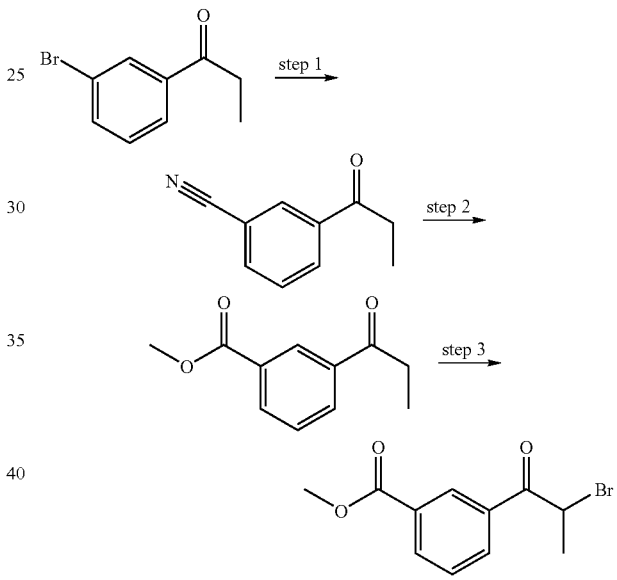

Step 1. 3-Bromopropriophenone (1.0 g, 4.7 mmol) was dissolved in dimethylformamide (3.5 mL) and treated with copper cyanide (0.55 g, 6.1 mmol). The resulting suspension was stirred under reflux for 6 h. After cooling back to room temperature, a freshly prepared solution of iron(III) chloride (0.47 g, 2.9 mmol) in water (3 mL) and fuming HCl 37% (1 mL) was added. The mixture was stirred at 80° C. for 20 min, then at room temperature overnight. The reaction mixture was diluted with little water (2 mL) and extracted with ether. The combined organic phases were washed with water and saturated sodium chloride, dried over sodium sulphate and evaporated. The residue was purified by flash chromatography (heptane/ethyl acetate gradient) to yield 3-propionyl-benzonitrile as a light yellow solid (0.62 g, 83%).

Step 2. 3-Propionyl-benzonitrile (0.61 g, 3.8 mmol) was refluxed in ethanol (5.3 mL) and KOH (0.48 g, 8.5 mmol) for 2 h. The ethanol was evaporated and the residue suspended in water (5 mL) and treated with 2N HCl (3.7 mL) to pH 1-2. The slurry was extracted with ethyl acetate. The combined organic phases were washed with water and saturated sodium chloride, dried over sodium sulphate and evaporated. The residue was dissolved in methanol (3.5 mL) and treated with 97% sulfuric acid (0.26 mL). The mixture was stirred at room temperature for 16 h, then at 70° C. for 7.5 h and at 50° C. for 16 h. After evaporation of methanol, the residue was suspended in water and extracted with ethyl acetate. The combined organic phases were washed with water and saturated sodium chloride, dried over sodium sulphate and evaporated. The residue was purified by flash chromatography (heptane/ethyl acetate gradient) to yield 3-propionyl-benzoic acid methyl ester as an off-white solid (0.42 g, 56%).

Step 3. A solution of 3-propionyl-benzoic acid-methyl ester (0.20 g, 1.1 mmol) in dichloromethane (2 mL) was cooled to 0° C. Bromine (0.17 g, 1.1 mmol) was added over 7 min. The mixture was stirred at room temperature for 2 h. Saturated sodium hydrogenocarbonate (2.7 mL) was added and the organic phase was separated, dried over sodium sulphate and evaporated. The residue was 3-(2-bromo-propionyl)-benzoic acid methyl ester (0.26 g, 79%), which was used without further purification.

Example 46

3-{5-Methyl-2-[(R)-1-(2-phenoxy-acetyl)-piperidin-2-yl]-thiazol-4-yl}-benzoic acid 3-{5-Methyl-2-[(R)-1-(2-phenoxy-acetyl)-piperidin-2-yl]-thiazol-4-yl}-benzoic acid, MS (ISP): 435.5 (M–H), was prepared as illustrated in example 40, using 3-{5-methyl-2-[(R)-1-(2-phenoxy-acetyl)-piperidin-2-yl]-thiazol-4-yl}-benzoic acid methyl ester (prepared as illustrated in example 45) as starting material.

Example A

Film coated tablets containing the following ingredients can be manufactured in a conventional manner:

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |

| | |
|---|---|
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

What is claimed is:

1. A compound of formula (I):

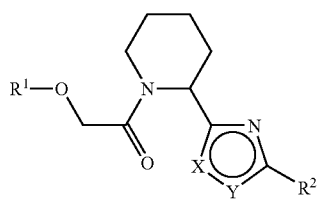

or a pharmaceutically acceptable salt or ester thereof, wherein:
X is sulfur and Y is —$CR^3$, or alternatively, X is —$CR^3$ and Y is sulfur; and $R^3$ is hydrogen, halogen, —CN, lower-alkyl, fluoro-lower-alkyl, lower-alkoxy, fluoro-lower-alkoxy or lower-alkoxy-lower-alkyl;
$R^1$ is aryl or heteroaryl, which aryl or heteroaryl can optionally be substituted with 1 to 3 substituents independently selected from the group consisting of halogen, hydroxy, —CN, lower-alkyl and hydroxy-lower-alkyl;
$R^2$ is aryl, heteroaryl or aryl-lower-alkyl, wherein said aryl or heteroaryl can optionally be substituted with 1 to 3 substituents independently selected from the group consisting of:
 (1) lower-alkyl, optionally substituted with hydroxy, —COOH, carbamoyl, amino, halogen or lower-alkoxy,
 (2) halogen,
 (3) hydroxy,
 (4) —CN,
 (5) —$NO_2$,
 (6) fluoro-lower-alkyl,
 (7) lower-alkoxy, optionally substituted with hydroxy, —COOH, carbamoyl, amino, halogen or lower-alkoxy,
 (8) fluoro-lower-alkoxy,
 (9) —$S(O_2)R^4$, wherein $R^4$ is lower-alkyl or amino;
 (10) —$C(O)R^5$, wherein $R^5$ is hydrogen, hydroxy, lower-alkyl, lower-alkoxy or amino;
 (11) imidazolyl,
 (12) pyrazolyl,
 (13) tetrazolyl,
 (14) pyrrolyl, and
 (15) —$NR^6R^7$, wherein $R^6$ and $R^7$, independently from each other, are selected from the group consisting of hydrogen, lower-alkyl, lower-alkyl-carbonyl and lower-alkyl-$SO_2$.

2. A compound of claim 1, wherein X is sulfur, Y is —$CR^3$ and $R^3$ is as defined in claim 1.

3. A compound of claim 1, wherein X is $CR^3$, Y is sulfur and $R^3$ is as defined in claim 1.

4. A compound of claim 1, wherein $R^1$ is phenyl.

5. A compound of claim 1, wherein $R^2$ is phenyl, benzyl or a heteroaryl selected from the group consisting of pyridinyl, 1,3-dihydroindolyl-2-one, benzo[1,3]dioxol-5-yl, indolyl, thienyl, indazolyl, pyrazinyl and 2,3-dihydro-benzo[1,4]dioxinyl; which said phenyl, benzyl or heteroaryl is optionally substituted with 1 to 3 substituents independently selected from the group consisting of lower-alkyl, halogen, hydroxy, CN, fluoro-lower-alkyl, lower-alkoxy, fluoro-lower-alkoxy, $S(O_2)R^4$, $C(O)R^5$ and $NR^6R^7$, wherein $R^4$, $R^5$, $R^6$ and $R^7$ are as defined in claim 1.

6. A compound of claim 1, wherein $R^2$ is phenyl or a heteroaryl selected from the group consisting of pyridinyl and 1,3-dihydroindolyl-2-one, which said phenyl or heteroaryl is optionally substituted with $C(O)R^5$ or $NR^6R^7$, wherein $R^5$, $R^6$ and $R^7$ are as defined in claim 1.

7. A compound of claim 1, wherein $R^2$ is 4-carboxy-phenyl, 3-carboxy-phenyl, 4-acetamide-phenyl, pyridin-2-yl, pyridin-3-yl, 1,3-dihydroindol-2-one-5-yl or 3-carboxy-pyridin-2-yl.

8. A compound of claim 1, wherein $R^3$ is hydrogen or lower-alkyl.

9. A compound of claim 1, wherein $R^3$ is hydrogen.

10. A compound of claim 1, wherein $R^4$ is lower-alkyl.

11. A compound of claim 1, wherein $R^5$ is hydroxy, lower-alkoxy or amino.

12. A compound of claim 1, wherein $R^5$ is hydroxy.

13. A compound of claim 1, wherein $R^6$ and $R^7$ independently from each other are hydrogen, lower-alkyl or lower-alkyl-carbonyl.

14. A compound of claim 1, wherein $R^6$ and $R^7$ independently from each other are hydrogen or lower-alkyl-carbonyl.

15. A compound of claim 1, wherein $R^6$ is hydrogen.

16. A compound of claim 1, wherein $R^7$ is acetyl.

17. A compound of claim 1, which is an R-enantiomer of formula (Ia):

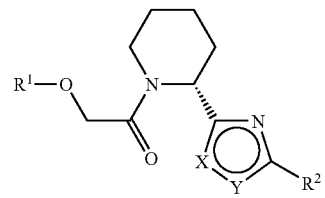

wherein $R^1$, $R^2$, X and Y are as defined in claim 1.

18. A compound of claim 1, selected from the group consisting of:
 1-{(R)-2-[4-(4-Chloro-phenyl)-thiazol-2-yl]-piperidin-1-yl}-2-phenoxy-ethanone,
 2-Phenoxy-1-[(R)-2-(4-phenyl-thiazol-2-yl)-piperidin-1-yl]-ethanone,
 4-{2-[(R)-1-(2-Phenoxy-acetyl)-piperidin-2-yl]-thiazol-4-yl}-benzoic acid,
 2-Phenoxy-1-{(R)-2-[4-(4-trifluoromethoxy-phenyl)-thiazol-2-yl]-piperidin-1-yl}-ethanone, 3-{2-[(R)-1-(2-Phenoxy-acetyl)-piperidin-2-yl]-thiazol-4-yl}-benzoic acid,
2-Phenoxy-1-[(R)-2-(4-pyridin-2-yl-thiazol-2-yl)-piperidin-1-yl]-ethanone,
1-{(R)-2-[4-(3,4-Difluoro-phenyl)-thiazol-2-yl]-piperidin-1-yl}-2-phenoxy-ethanone,
2-Phenoxy-1-[(R)-2-(4-pyridin-3-yl-thiazol-2-yl)-piperidin-1-yl]-ethanone,
1-{(R)-2-[4-(5-Chloro-2-methoxy-phenyl)-thiazol-2-yl]-piperidin-1-yl}-2-phenoxy-ethanone,
2-Phenoxy-1-[(R)-2-(4-pyridin-4-yl-thiazol-2-yl)-piperidin-1-yl]-ethanone,
1-{(R)-2-[4-(2-Methoxy-phenyl)-thiazol-2-yl]-piperidin-1-yl}-2-phenoxy-ethanone,
1-{(R)-2-[4-(4-Methanesulfonyl-phenyl)-thiazol-2-yl]-piperidin-1-yl}-2-phenoxy-ethanone,
6-{2-[(R)-1-(2-Phenoxy-acetyl)-piperidin-2-yl]-thiazol-4-yl}-pyridine-2-carboxylic acid methyl ester,
5-{2-[(R)-1-(2-Phenoxy-acetyl)-piperidin-2-yl]-thiazol-4-yl}-1,3-dihydro-indol-2-one,
N-(4-{2-[(R)-1-(2-Phenoxy-acetyl)-piperidin-2-yl]-thiazol-4-yl}-phenyl)-acetamide,
1-{(R)-2-[4-(4-Hydroxy-phenyl)-thiazol-2-yl]-piperidin-1-yl}-2-phenoxy-ethanone,
1-[(R)-2-(4-Benzo[1,3]dioxol-5-yl-thiazol-2-yl)-piperidin-1-yl]-2-phenoxy-ethanone,
1-{(R)-2-[4-(4-Dimethylamino-phenyl)-thiazol-2-yl]-piperidin-1-yl}-2-phenoxy-ethanone,
1-{(R)-2-[4-(3-Methyl-1H-indol-2-yl)-thiazol-2-yl]-piperidin-1-yl}-2-phenoxy-ethanone,
4-{2-[(R)-1-(2-Phenoxy-acetyl)-piperidin-2-yl]-thiazol-4-yl}-benzonitrile,
3-{2-[(R)-1-(2-Phenoxy-acetyl)-piperidin-2-yl]-thiazol-4-yl}-benzonitrile,
1-{(R)-2-[4-(6-Chloro-pyridin-3-yl)-thiazol-2-yl]-piperidin-1-yl}-2-phenoxy-ethanone,
1-{(R)-2-[4-(5-Bromo-thiophen-2-yl)-thiazol-2-yl]-piperidin-1-yl}-2-phenoxy-ethanone,
3-{4-[(R)-1-(2-Phenoxy-acetyl)-piperidin-2-yl]-thiazol-2-yl}-benzoic acid methyl ester,
N-(4-{4-[(R)-1-(2-Phenoxy-acetyl)-piperidin-2-yl]-thiazol-2-yl}-phenyl)-acetamide,
1-{(R)-2-[2-(1H-Indazol-3-yl)-thiazol-4-yl]-piperidin-1-yl}-2-phenoxy-ethanone,
2-Phenoxy-1-{(R)-2-[2-(6-trifluoromethyl-pyridin-3-yl)-thiazol-4-yl]-piperidin-1-yl}-ethanone,
2-Phenoxy-1-{(R)-2-[2-(5-trifluoromethyl-pyridin-2-yl)-thiazol-4-yl]-piperidin-1-yl}-ethanone,
2-Phenoxy-1-[(R)-2-(2-pyrazin-2-yl-thiazol-4-yl)-piperidin-1-yl]-ethanone,
1-{(R)-2-[2-(6-Methyl-pyridin-3-yl)-thiazol-4-yl]-piperidin-1-yl}-2-phenoxy-ethanone,
2-Phenoxy-1-[(R)-2-(2-pyridin-3-yl-thiazol-4-yl)-piperidin-1-yl]-ethanone,
2-Phenoxy-1-[(R)-2-(2-pyridin-4-yl-thiazol-4-yl)-piperidin-1-yl]-ethanone,
1-{(R)-2-[2-(6-Methoxy-pyridin-3-yl)-thiazol-4-yl]-piperidin-1-yl}-2-phenoxy-ethanone,
2-Phenoxy-1-[(R)-2-(2-pyridin-2-yl-thiazol-4-yl)-piperidin-1-yl]-ethanone,
1-{(R)-2-[2-(4-Fluoro-phenyl)-thiazol-4-yl]-piperidin-1-yl}-2-phenoxy-ethanone,
4-{4-[(R)-1-(2-Phenoxy-acetyl)-piperidin-2-yl]-thiazol-2-yl}-benzoic acid methyl ester,
1-{(R)-2-[2-(4-Chloro-benzyl)-thiazol-4-yl]-piperidin-1-yl}-2-phenoxy-ethanone,
1-{(R)-2-[2-(2,3-Dihydro-benzo[1,4]dioxin-2-yl)-thiazol-4-yl]-piperidin-1-yl}-2-phenoxy-ethanone,
4-{2-[(R)-1-(2-Phenoxy-acetyl)-piperidin-2-yl]-thiazol-4-yl}-benzamide,
3-{4-[(R)-1-(2-Phenoxy-acetyl)-piperidin-2-yl]-thiazol-2-yl}-benzoic acid,
4-{4-[(R)-1-(2-Phenoxy-acetyl)-piperidin-2-yl]-thiazol-2-yl}-benzoic acid,
6-{2-[(R)-1-(2-Phenoxy-acetyl)-piperidin-2-yl]-thiazol-4-yl}-pyridine-2-carboxylic acid,
Sodium; 4-{2-[(R)-1-(2-phenoxy-acetyl)-piperidin-2-yl]-thiazol-4-yl}-benzoate,
Sodium; 3-{2-[(R)-1-(2-phenoxy-acetyl)-piperidin-2-yl]-thiazol-4-yl}-benzoate,
3-{5-Methyl-2-[(R)-1-(2-phenoxy-acetyl)-piperidin-2-yl]-thiazol-4-yl}-benzoic acid methyl ester and,
3-{5-Methyl-2-[(R)-1-(2-phenoxy-acetyl)-piperidin-2-yl]-thiazol-4-yl}-benzoic acid,
or a pharmaceutically acceptable salt or ester thereof.

19. A compound of claim 1, selected from the group consisting of:
4-{2-[(R)-1-(2-Phenoxy-acetyl)-piperidin-2-yl]-thiazol-4-yl}-benzoic acid,
3-{2-[(R)-1-(2-Phenoxy-acetyl)-piperidin-2-yl]-thiazol-4-yl}-benzoic acid,
2-Phenoxy-1-[(R)-2-(4-pyridin-2-yl-thiazol-2-yl)-piperidin-1-yl]-ethanone,
2-Phenoxy-1-[(R)-2-(4-pyridin-3-yl-thiazol-2-yl)-piperidin-1-yl]-ethanone,
5-{2-[(R)-1-(2-Phenoxy-acetyl)-piperidin-2-yl]-thiazol-4-yl}-1,3-dihydro-indol-2-one,
N-(4-{2-[(R)-1-(2-Phenoxy-acetyl)-piperidin-2-yl]-thiazol-4-yl}-phenyl)-acetamide,
2-Phenoxy-1-[(R)-2-(2-pyridin-3-yl-thiazol-4-yl)-piperidin-1-yl]-ethanone,
3-{4-[(R)-1-(2-Phenoxy-acetyl)-piperidin-2-yl]-thiazol-2-yl}-benzoic acid,
6-{2-[(R)-1-(2-Phenoxy-acetyl)-piperidin-2-yl]-thiazol-4-yl}-pyridine-2-carboxylic acid and,
3-{2-[(R)-1-(2-Phenoxy-acetyl)-piperidin-2-yl]-thiazol-4-yl}-benzoate sodium salt,
or a pharmaceutically acceptable salt or ester thereof.

20. A process for the manufacture of compounds of formula (I) as defined in claim 1, which process comprises reacting a compound of formula (IV):

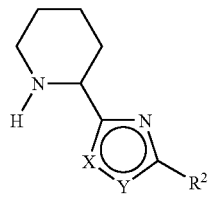

with a compound of formula $R^1$—O—$CH_2$—C(O)Cl, wherein $R^1$, $R^2$, X and Y are as defined in claim 1.

21. A pharmaceutical composition comprising a therapeutically effective amount of a compound of claim 1 and a pharmaceutically acceptable carrier.

* * * * *